(12) United States Patent
Hamilton (10) Patent No.: US 12,408,807 B2
(45) Date of Patent: Sep. 9, 2025

(54) STRUCTURE FOR APPLYING ANTIMICROBIAL MATERIAL TO A CABLE

(71) Applicant: Grant James Hamilton, Pompano Beach, FL (US)

(72) Inventor: Grant James Hamilton, Pompano Beach, FL (US)

( * ) Notice: Subject to any disclaimer, the term of this patent is extended or adjusted under 35 U.S.C. 154(b) by 40 days.

(21) Appl. No.: 18/655,785

(22) Filed: May 6, 2024

(65) Prior Publication Data
US 2024/0366822 A1   Nov. 7, 2024

Related U.S. Application Data

(60) Provisional application No. 63/464,323, filed on May 5, 2023.

(51) Int. Cl.
| | |
|---|---|
| A47L 13/17 | (2006.01) |
| A61B 50/24 | (2016.01) |
| A61B 90/70 | (2016.01) |
| A61L 2/235 | (2006.01) |
| B05C 1/06 | (2006.01) |

(52) U.S. Cl.
CPC ............. *A47L 13/17* (2013.01); *A61B 90/70* (2016.02); *A61L 2/235* (2013.01); *B05C 1/06* (2013.01); *A61B 50/24* (2016.02); *A61L 2202/15* (2013.01); *A61L 2202/24* (2013.01)

(58) Field of Classification Search
CPC ..... A61B 90/70; A61L 2202/24; A61L 2/235; A47L 13/17; A47L 13/26; A47L 25/00; B05C 1/06

USPC ............................. 15/104.04, 104.92–104.94
See application file for complete search history.

(56) References Cited

U.S. PATENT DOCUMENTS

| | | | | |
|---|---|---|---|---|
| 946,370 | A * | 1/1910 | Kelmel ................... | A46B 9/02 15/160 |
| 2,255,154 | A * | 9/1941 | Esposito ............... | D06F 53/005 401/9 |
| 2,604,650 | A * | 7/1952 | Mottelson ............. | D06F 53/005 15/220.4 |
| 2,821,730 | A * | 2/1958 | Shellman ................ | E21B 33/08 254/389 |
| 4,084,287 | A * | 4/1978 | Ingram .................. | A63B 47/04 15/21.2 |
| 5,242,428 | A * | 9/1993 | Palestrant ............. | A61M 25/01 604/265 |
| 5,334,166 | A * | 8/1994 | Palestrant ............. | A61M 25/01 604/265 |
| 5,382,297 | A * | 1/1995 | Valentine ............... | A61B 1/127 15/210.1 |
| 5,647,084 | A * | 7/1997 | Still .......................... | B08B 1/12 15/40 |
| 8,196,248 | B2 * | 6/2012 | Kritzler ................ | C11D 17/041 15/115 |
| 9,693,833 | B2 * | 7/2017 | Mottola ................ | A61B 90/70 |

(Continued)

*Primary Examiner* — Laura C Guidotti
(74) *Attorney, Agent, or Firm* — The Concept Law Group, PA; Scott D. Smiley; Scott M. Garrett (57) ABSTRACT

A puck is made of a porous resilient material and is held in a housing to comprise a cable swipe cassette. The puck holds fluid in the porous material, and there is a bore through the puck. A cable is routed through the bore so that when the cable is pulled through the bore the exterior surface of the cable is wetted with the fluid. The fluid can have an antimicrobial effect so as to disinfect the cable.

14 Claims, 12 Drawing Sheets

(56) References Cited

U.S. PATENT DOCUMENTS

| | | | |
|---|---|---|---|
| 11,759,287 B2* | 9/2023 | Patel | A61B 90/40 |
| | | | 118/200 |
| 11,813,125 B2* | 11/2023 | Brody | B08B 1/14 |
| 2024/0246120 A1* | 7/2024 | Brewer | B08B 11/00 |

* cited by examiner

STRUCTURE FOR APPLYING ANTIMICROBIAL MATERIAL TO A CABLE

CROSS REFERENCE

This application claims priority to U.S. provisional application No. 63/464,323, filed May 5, 2023, the entirety of which is hereby incorporated by reference.

FIELD OF THE INVENTION

The present invention relates generally to medical equipment, and, more particularly, relates to a structure or device that applies antimicrobial material to cables used for medical devices, and specifically to a device that holds a puck or similar article that has a hole through it, wherein the medical device cable is routed through the hole in the puck. The puck contains antimicrobial material, and when the cable is pulled through the puck, such as for use in measuring a biometric parameter, some of the antimicrobial material is transferred to the outer surface of the cable, thereby killing microbes on the outer surface of the cable.

BACKGROUND OF THE INVENTION

It is well known that in the provision of medical services, it is imperative to prevent exposing a patient to infectious microbes. There are numerous surfaces and instruments that patients come in contact with in a medical facility that can impart undesirable microbes to the patient through contact with those items. While routine cleaning practices can reduce the incidence of infectious microbes, some surfaces, like floors, are frequently being contaminated simply through ordinary usage (e.g. people walking on them with dirty shoes). Another surface that is easily contaminated, and often overlooked for cleaning, are the cables used with medical instruments. These are often overlooked, and can come into contact with various other surfaces, including floors. Given how often medical instruments are used, and moved from patient to patient, they present a likely infection vector. Cables are often placed on the patient during use, and therefor come into contact with the garments worn by the patient, who also may make contact with any material left on the garment from the cables. In some cases, the patient can come into direct contact with the cables. Even if carefully kept from coming into contact with potentially unclean surfaces, such as a floor, the cables can come into contact with multiple patients, who may have an infection or unknowingly have infectious material on their clothing. Thus, cables of medical devices present a significant potential for transmitting infectious agents. Cable can be cleaned by personnel by, for example, spraying the cables with a disinfecting agent and then wiping them down, but this adds to the tasks needed to be performed by personnel, and in practice, it is often foregone as a matter of convenience.

Therefore, a need exists to overcome the problems with the prior art as discussed above.

SUMMARY

In accordance with some embodiments of the inventive disclosure, there is provided a cable swipe cassette which includes a puck made of a porous resilient material. The puck has a bore from a first side to a second side opposite the first side. There is also a housing that encloses the puck therein. The housing has openings on opposite sides of the housing that correspond with the bore.

In accordance with a further feature, the housing is hinged and has an upper portion and a lower portion coupled together at a hinge.

In accordance with a further feature, the housing has a latch opposite the hinge to latch the upper and lower portions of the housing together.

In accordance with a further feature, there is also includes a fluid disposed in the puck.

In accordance with a further feature, the fluid is an antimicrobial fluid.

In accordance with a further feature, the puck further comprises a slot extending outward from the bore to a cylindrical surface of the puck.

In accordance with some embodiments of the inventive disclosure, there is provided a stand for a medical device that includes a cable retracting mechanism disposed on the stand. There is a cable disposed on the cable retracting mechanism that has a first end that is configured to attach to a signal input of the medical device and a second end that is configured to attach to a sensor. There is also a cable swipe that includes a holder that can be opened. The holder has opposing walls, and each of the opposing walls has an opening through them. There is a puck configured to be disposed in the holder. The puck made of a material configured to hold an antimicrobial fluid and has a bore through it that, when the puck is placed in the holder, aligns with the openings in the opposing walls of the holder. The bore through the puck has a smaller diameter than an exterior diameter of the cable. The puck further has a slot from a cylindrical surface of the puck to the bore though the puck. The second end of the cable passes through the bore of the puck such that when the cable is drawn through the puck an exterior of the cable is wetted by the antimicrobial fluid. There is also a support mounted on the stand that is configured to support the holder while the holder is holding the puck and while the cable passes through the puck.

In accordance with a further feature, the puck is made of a porous resilient material.

In accordance with a further feature, the puck is selected from a plurality of pucks that have different sized bores.

In accordance with a further feature, the stand comprises casters in order to make the stand mobile.

In accordance with some embodiments of the inventive disclosure, there is provided a cable disinfecting mechanism that includes a cable reel. The cable reel has a cable wound on a reel. The cable reel has a cable outlet through which one end of the cable passes. There is also a cable swipe cassette assembly mounted at the cable outlet. The cable swipe cassette assembly has a housing and a puck inside the housing. The puck is made of a resilient porous material and has a bore through it. There is an antimicrobial fluid disposed in the puck. The one end of the cable passes through the bore of the puck such that when the cable is drawn through the puck an exterior surface of the cable is wetted with the antimicrobial fluid.

In accordance with a further feature, the puck includes a slot that passes through a side of the puck to the bore.

In accordance with a further feature, the housing of the cable swipe cassette assembly is configured to clamp onto the cable reel at the cable outlet.

In accordance with a further feature, the cable reel is mounted on a stand for a medical device.

In accordance with a further feature, the housing of the cable swipe cassette assembly is hinged and has an upper portion and a lower portion coupled together at a hinge.

In accordance with a further feature, the housing has a latch opposite the hinge to latch the upper and lower portions of the housing together.

Although the invention is illustrated and described herein as embodied in a structure for applying antimicrobial material to cables for medical devices, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

To solve the problem of medical device cables becoming fouled with potentially infectious agents, a cable swipe is provided that includes a load of antimicrobial material. The cable is drawn through the cable swipe, and contact between the cable and the cable swipe material results in the antimicrobial material wetting the outer surface of the cable along the length of the cable that is drawn through the cable swipe, thereby disinfecting that portion of the cable. Furthermore, in conjunction with the pull-through cable swipe structure, the cable can be provided on a reel so that when the cable is reeled in after use, the cable will again be wetted with the antimicrobial material, and the wetted portion of the cable will be in contact with some portions of the cable that were not drawn through the cable swipe, thereby imparting antimicrobial material to those portions of the cable as well.

Figure 1:
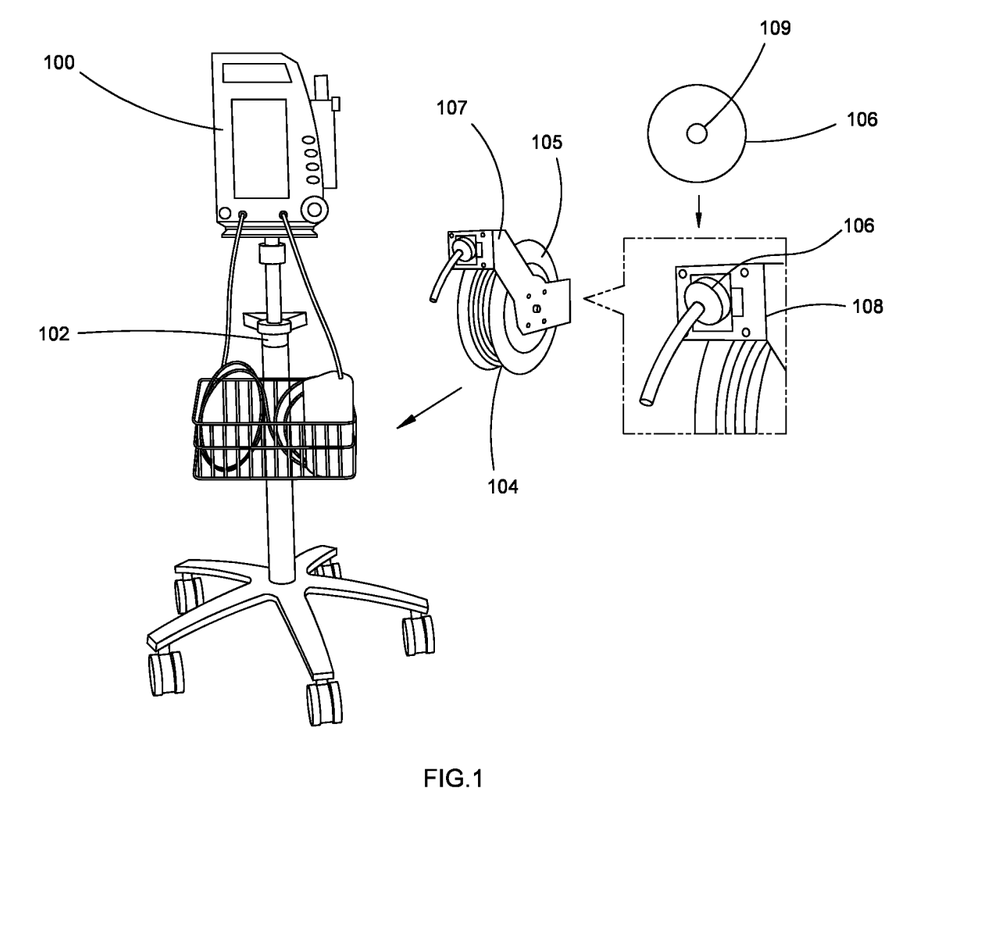
FIG. 1 shows a medical device on a stand for use in a medical facility wherein the stand includes a disinfecting cable swipe through which the cable is fed so that every time a cable is drawn through the cable swipe a new application of antimicrobial material is applied to the exterior of the cable.

FIG. 1 shows a medical device 100 on a stand 102 for use in a medical facility, wherein the stand 102 that holds the medical device 100 can include casters, wheels, or rollers at the bottom of the stand 102 to make the stand 102 and medical device 100 portable so that it can be moved from patient to patient. That is, the medical device 100 can be moved from patient to patient, as needed, to either provide some medical treatment to the patient or to measure and monitor some physiological and medically significant parameter of the patient. The medical device 100 uses one or more cables such as cable 104 to connect between the medical device 100 and a sensor or actuator at or on the patient. Electrical signals are transmitted through the cable 104 either by or to the medical device 100. Cable 104 is shown here on a cable retracting mechanism such as, for example reel 105 that is held by a reel holder 107 that can mount on the stand 102. The cable 104 has a portion that is wound around the reel 105, and a portion that is static which connects to the medical device 100. An end of the cable 104 is fed through a disinfecting cable swipe 106 that is mounted at the outlet of the reel 105 on the reel holder 107. The cable 104 is fed through the cable swipe 106 so that every time the cable 104 is drawn through the cable swipe 106 a new application of antimicrobial material is applied to the exterior of the cable 104. The reel 105 can be self-reeling so that when the medical device 100 is no longer needed for a given patient, the reel 105 can self-wind the cable 104 back onto the reel 105. The cable swipe 106 is a cassette that includes a puck that can be made of a resilient porous material that is saturated with an antimicrobial fluid. The cable swipe 106, including the puck held in a case or housing, can be mounted at the outlet of the reel 105 on the reel holder 107. The reel holder 107 can be attached to the stand 102 by any conventional attachment means, including a bolted bracket, a slip-on attachment, straps, and so on. In some cases, the reel 105 and reel holder 107 can be permanently mounted on the stand 102.

As a result of being moved from patient to patient, the cable 104 can come into contact with various objects, including a patient, the floor, the hands of various nurses and other healthcare workers, and so on. As a result, there is a significant chance of some microbial agent being introduced to the outside surface of the cable 104. By drawing the cable 104 through the cable swipe 106 each time it is to be used, and each time it is reeled back up, the outside of the cable 104 is repeatedly treated with the antimicrobial material. There are a wide variety of disinfecting materials that are known and which can be carried and applied by the cable swipe 106.

As mentioned, one end of the cable 104 extends out of the reel 105 and attaches to a signal input of the medical device 100. The other end of the cable 104 is intended to be attached to a sensor on a patient, and is fed off the reel 105 through the cable swipe 106, which is held in a cable swipe support 108 that can be mounted on the reel holder 107. The cable swipe 106 can include, for example a puck or an annular sponge member that has an opening 109 through which the cable 104 passes. The opening 109 is sized to be slightly smaller than the exterior diameter of the cable 104 to ensure that the cable swipe 106 will be in contact with the exterior of the cable 104 so as to impart the antimicrobial material to the outside of the cable 104. The cable swipe 106 can be made of a porous resilient material that contains or holds the antimicrobial fluid.

Figure 2:
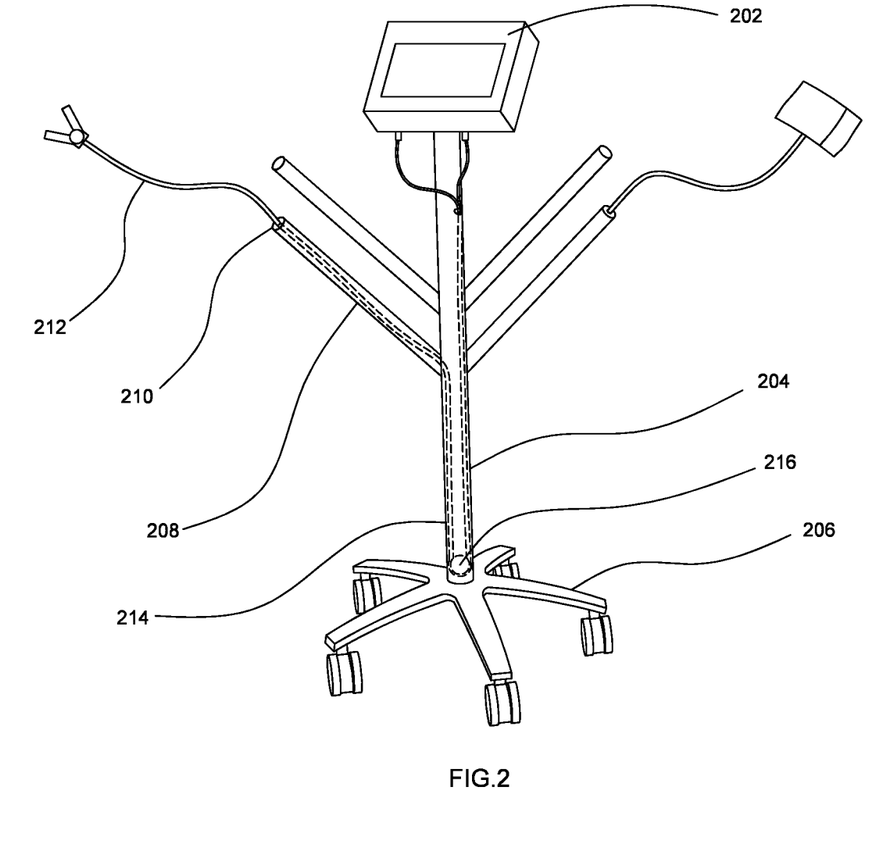
FIG. 2 shows an alternate example of a medical device on a stand for use in a medical facility wherein the stand includes a disinfecting cable swipe through which the cable is fed so that every time a cable is drawn through a cable swipe a new application of antimicrobial material is applied to the exterior of the cable.

FIG. 2 shows an alternate example of a medical device 202 on a stand 204 for use in a medical facility wherein the stand 204 includes a disinfecting cable swipe 210 through which a cable 212 is fed so that every time a cable is drawn through a cable swipe 210 a new application of antimicrobial material is applied to the exterior of the cable 212. The stand 204 can include a wheeled base 206 so as to be mobile. A reel or other cable retracting mechanism 214 can be contained in or on the stand 204 that the cable 212 can be locked in position once the cable 212 is fed out to a desired length through a guide 208, and then unlocked to reel in the cable 212. The guides 208 are configured to support the puck in the cable swipe as well as guide the cable out of and into the cable retracting mechanism. The guides can be, for example, tubular arms that extend from a central post of the stand 204. The cable retracting mechanism 214 can include a pulley 216 around which the cable 212 is routed, and as the cable 212 is pulled out, through the cable swipe 210, the pulley 216 rises inside or on the outside of the stand 204, and may be biased downward by a spring, or simply its own weight. The position of the pulley 216 can be locked in place once the desired length of cable 212 is fed out, and then released to draw the cable back into the stand 204. When the cable 212 is drawn back into the stand 204 by the pulley 216 being urged downward, more of the antimicrobial fluid is swiped onto the exterior surface of the cable 212. Thus, as the cable 212 travels in both directions (being fed out, and then reeled in) it passes through the cable swipe 210, which is substantially similar to cable swipe 106. The cable swipe 210 can be changed out periodically to ensure that there is sufficient wetting of the exterior of the cable 212 with the antimicrobial fluid from the cable swipe 210.

Figure 3:
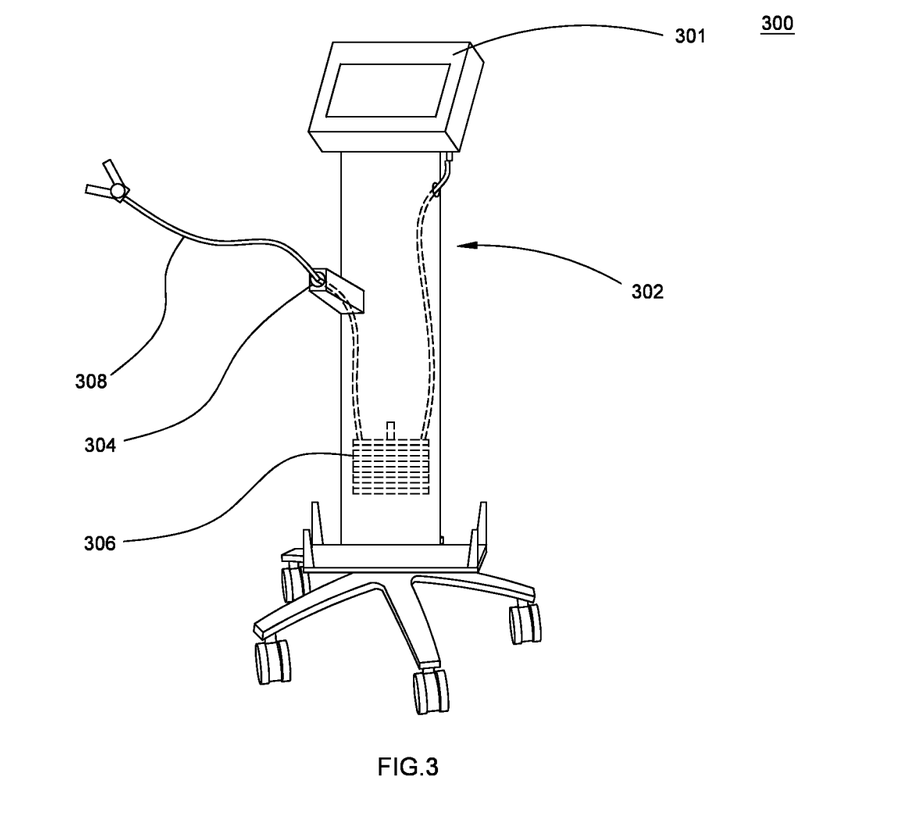
FIG. 3 shows another alternative example medical device on a stand for use in a medical facility wherein the stand includes a disinfecting cable swipe through which the cable is fed so that every time a cable is drawn through a cable swipe a new application of antimicrobial material is applied to the exterior of the cable.

FIG. 3 shows another alternative example medical device system 300 in which a medical device 301 is positioned on a stand 302 for use in a medical facility wherein the stand 302 includes a disinfecting cable swipe 304 through which a cable 308 is fed from a reel 306 so that every time the cable 308 is drawn through the cable swipe 304 a new application of antimicrobial material is applied to the exterior of the cable 308. Similar to FIG. 2, the medical device stand 302 supports or otherwise includes reel 306. The reel 306 can be spring driven to automatically take up slack in the cable 308, or it can be manually driven. An internal end of the cable 308 is attached to a signal input of the medical device 301, and the other end is fed out through the cable swipe 304 and can be attached to a sensor on the patient. In this embodiment the reel 306 can be housed internally in the stand 302 or externally as in FIG. 1. A in the previous examples, the stand 302 is mobile by having a plurality of casters or wheels at the bottom of the stand 302 on which the stand 302 can roll about.

Figure 4:
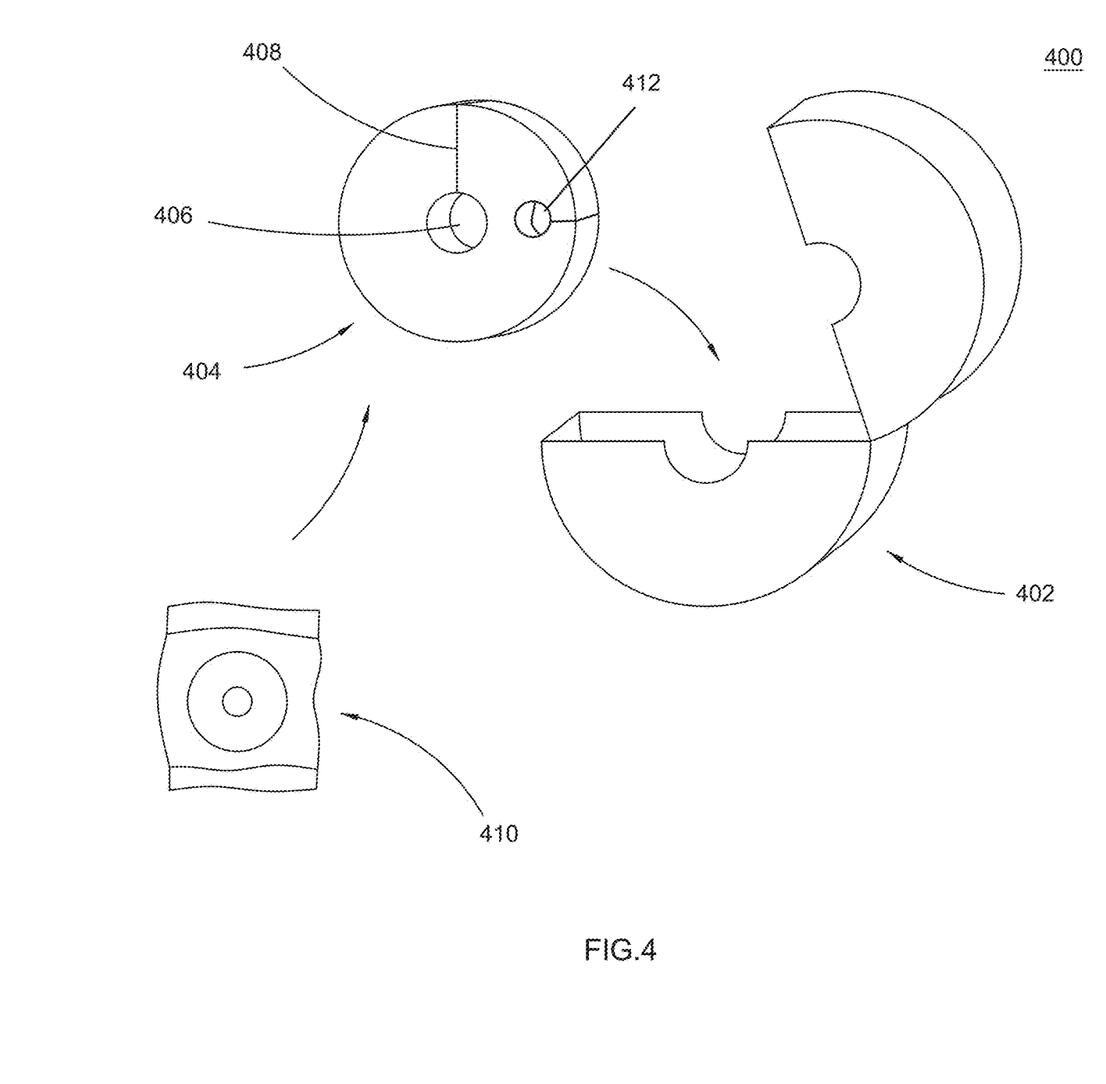
FIG. 4 shows a cable swipe cassette assembly, in accordance with some embodiments.
Figure 12:
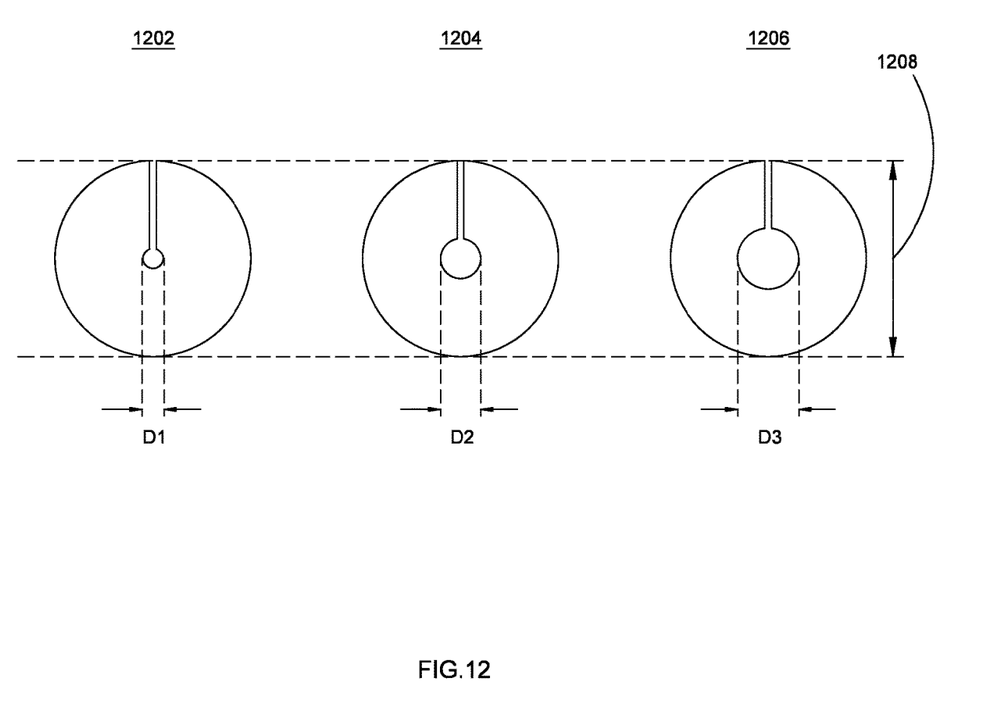
FIG. 12 shows a series of several cable swipes that all fit in the same cassette but which accommodate cables of different sizes, in accordance with some embodiments.

FIG. 4 shows a cable swipe cassette assembly 400, in accordance with some embodiments. The assembly 400 can include a holder 402 that is configured to hold a puck 404. The puck 404 is a portion of material that can hold a volume of antimicrobial fluid. The puck material can be, for example, fabric, open cell resilient foam, or any other suitably resilient and porous material. In general, the material of the puck 404 can be such that capillary action between the antimicrobial fluid and the material of the puck helps to retain the fluid in the puck 404. The puck 404 has an opening 406 through it that aligns with similar openings in the sides of the holder 402. The puck 404 has a cut 408 from the outside of the puck 404 to the opening 406 that allows a user to push a cable through so that the cable sits in the opening 406. As described, the opening 406 is sized so that there is constant contact between the material of the puck 404 and the cable as the cable is drawn back and forth through the opening 406. Thus, as indicated in FIG. 12, there can be a variety of pucks 404 that all have different sized openings 406 to accommodate different sizes of cables. The holder 402 ensures that the fluid held in the puck 404 doesn't drip out, as well as providing mechanical support for the puck 404. The holder 402 can be mounted in or on another structure on the stand holding the medical device. The puck 404 can be individually packaged 410 so that, when a puck is depleted of the microbial fluid, it can be easily replaced with a new puck. To replace the puck, the holder 402 is opened, the old puck removed from both the holder 402 and the cable, then the new puck is removed from the packaging 410 and placed in the holder, and the cable is placed into the opening 406 of the new puck by passing the cable through the cut 408, and then the holder 402 can be closed. The holder 402 can be made of a rigid, fluid impermeable material, and is supported by structure on the stand, such as a tube, guide, reel, or other mounting apparatus that is configured to hold the holder 402, puck 404, and cable for use.

Figure 5:
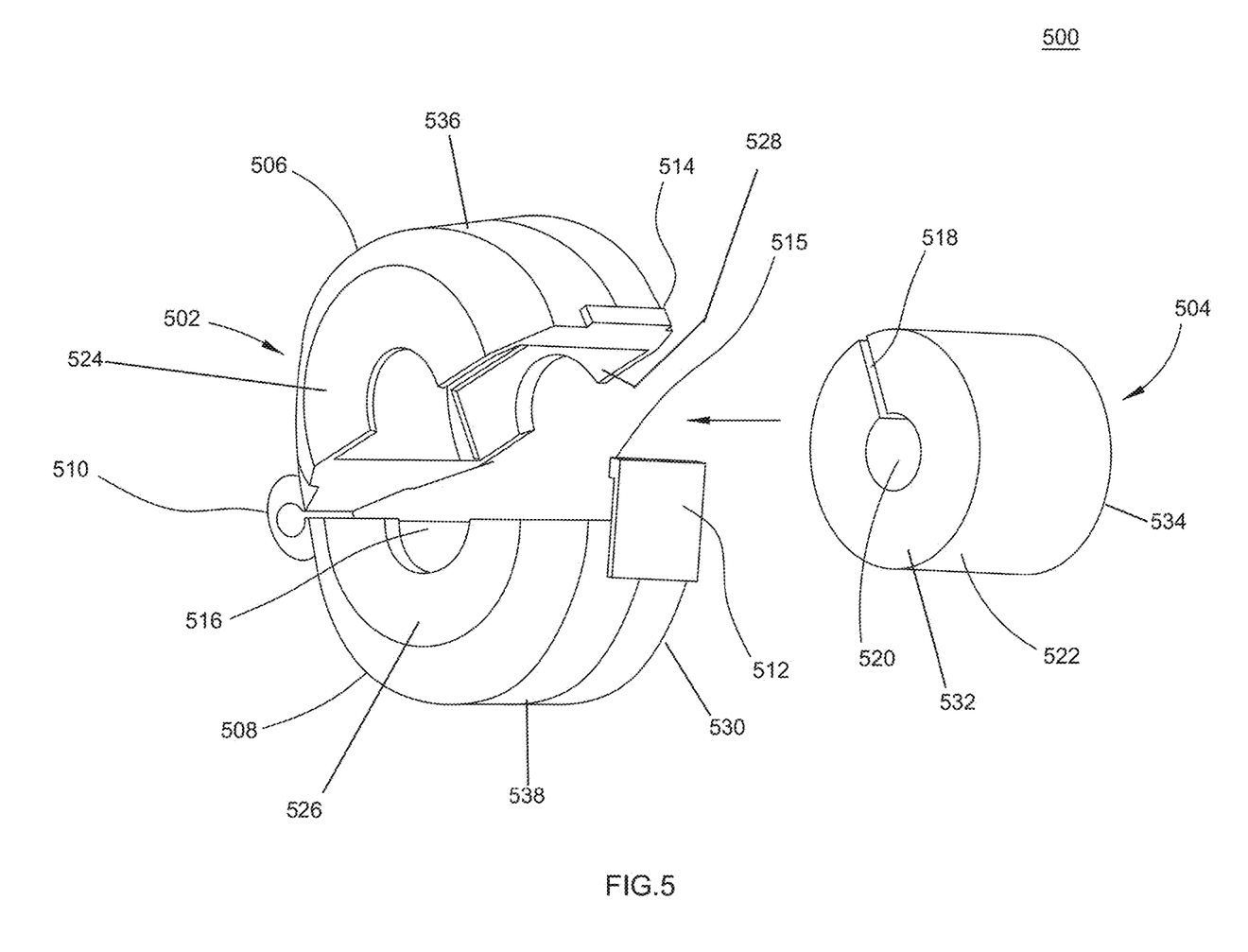
FIG. 5 shows an alternative cable swipe cassette assembly having a latch, in an open configuration, in accordance with some embodiments.
Figure 6:
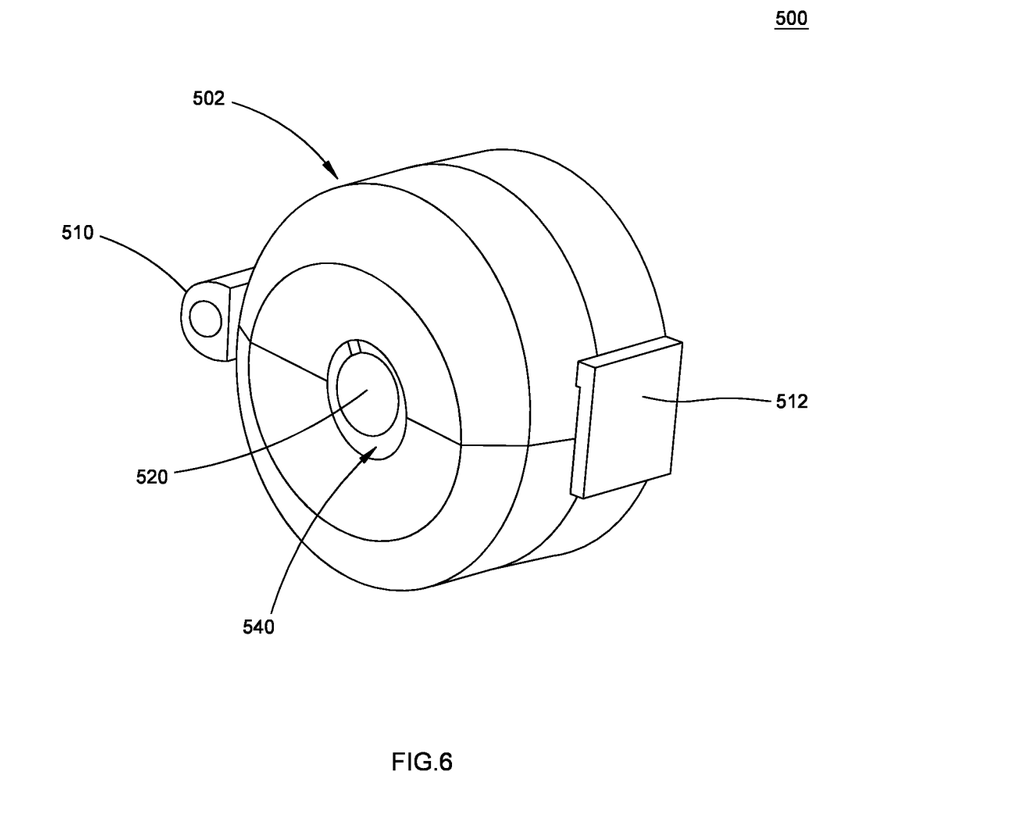
FIG. 6 shows an alternative cable swipe cassette assembly having a latch, in a closed configuration, in accordance with some embodiments.

FIG. 5 shows an alternative cable swipe cassette assembly 500 having a latch 512, in an open configuration, and FIG. 6 shows the same assembly 500 in a closed configuration, in accordance with some embodiments. The assembly 500 includes a puck housing or holder 502 and the puck 504 which sits inside the holder 502. The holder 502 can be a "clamshell" type container that has an upper portion 506 and a lower portion 508 that are joined by a hinge 510 so that the holder encloses the puck 504. The holder 502 is somewhat puck-shaped itself, and upper and lower portions 506, 508 can each have a semi cylindrical shape to accommodate the puck 504, which has a cylindrical shape, inside the holder 502. The upper portion 506 has a first side 524 and a second side 528, and the lower portion 508 likewise has a first side 526 and a second side 530. The first sides 524, 526 could be considered a front side of the housing, and the second sides 528, 530 could be considered a back side of the housing when the housing portions 506, 508 are closed together. The upper portion 506 includes a transverse wall 536 between the first side 524 and the second side 528 that forms half of the outside circumference of the holder 502. Likewise, the lower portion 508 has a transverse wall 538 between the first side 526 and the second side 530 of the lower portion 508 that forms the complementary half of the outside circumference of the holder 502 when the upper and lower portions 506, 508 are closed together. The puck 504 sits in the housing 502 between the first sides 524, 526 and the second sides 528, 530, and surrounded around cylindrical side 522 by the transverse walls 536, 538 of the upper and lower portions 506, 508. That is, the puck 504 occupies a space between the first side 524 and the second side 528 of the upper portion 506, and between the first side 526 and the second side 530 of the lower portion 508 of the housing 502 and within the transverse walls 536, 538. Thus, when placed into the housing/holder 502, a first side 532 of the puck 504, which is one of the two flat surfaces 532, 534 of the puck 504, will be adjacent the first side 524 of the upper portion 506 and the first side 526 of the lower portion 508 inside the holder 502. Likewise, the second side 534 of the puck 504 will be adjacent the second side 528 of the upper portion 506 and the second side 530 of the lower portion 508 while inside the holder/housing 502. There can be a latch member 512 that interfaces with a retention feature 514 to hold the holder closed, but allow a user to open the holder by disengaging the latch 512 from the retention member 514. The latch is on the lower portion 508, opposite the hinge 510, and extends upward so as to be able to engage the retention member 514, which is also opposite the hinge on the upper portion 506. When the holder 502 is closed, the upper end of the latch member 512 is pushed outward by the retention member 514 as the retention member 514 moves past a retaining lip 515. Once the retaining member 514 is past the retaining lip 515 the retaining lip 515 will move back toward the center of the holder, thereby creating a mechanical interference between the retaining member 514 and the retaining lip 515, holding the holder portions 506, 508 closed. When a user wants to open the holder 502, to insert a puck 504, the upper end of the latch member 512 can be biased outward by the user's fingers, allowing the retaining member 514 to move past the retaining lip 515 in the upward or opening direction. The holder 502 has openings on opposite sides or opposite/opposing s walls that correspond to the location of the bore through the puck 504.

The puck 504 is made of a resilient porous material that can hold an antimicrobial fluid. Furthermore, the puck 504 has a bore 520 through the puck in the axial direction of the puck 504. That is, the puck has a cylindrical shape, and the axial direction is from one end to the opposite end of the cylinder-shaped body. There is also a slot 508 cut into the puck from the outside along the side of the puck 504 to the bore 520. This allows a user to press or push a cable through the slot 518 into the bore 520, thereby capturing the cable in the bore 520. With the cable captured in the bore, the puck 504 can then be placed into the holder 502, and the holder 502 then closed. Thereafter, when the cable is drawn trough the puck, in either direction, some of the antimicrobial fluid carried by the puck can be imparted to the cable. The cable will the pass through the openings 540 on the first and second sides of the holder 502. The openings 540 can be circular and formed when the holder/housing 502 is closed by semicircular cutouts 516 formed along the edges of the first sides 524, 526 where the first side 524 of the upper portion 506 meets the first side 526 of the lower portion 508 when the holder 502 is closed, and at the edges of the second sides 528, 530 where the second side 528 of the upper portion 506 meets the second side 5306 of the lower portion 508 when the holder 502 is closed. The holder 502, when closed, can slight compress the puck 504 so as to prevent the cable from becoming seated in the slot 518.

The puck, as shown as puck 404 and puck 504, can be a generally right cylinder-shaped object with opposing planar ends 532, 534, and a cylindrical side 522. The slot 408, 518 can pass from end to end along the bore, and extend from the bore outward to the cylindrical surface. The bore can run through the central of the puck, but it is also contemplated that there can be more than one bore through the puck so that multiple cables can be run through the same puck, with each bore having its own slot to allow a cable to be placed into the respective bore.

Figure 7:
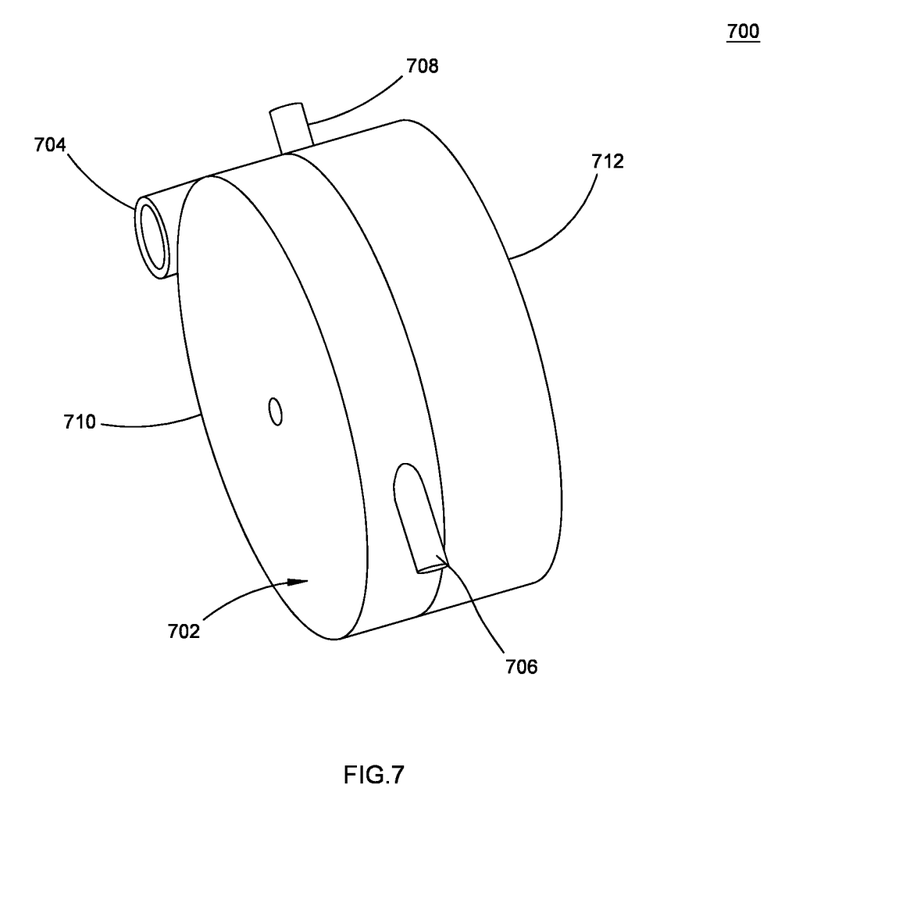
FIG. 7 shows a cable reel housing for use with a cable swipe cassette assembly, in accordance with some embodiments.
Figure 8:
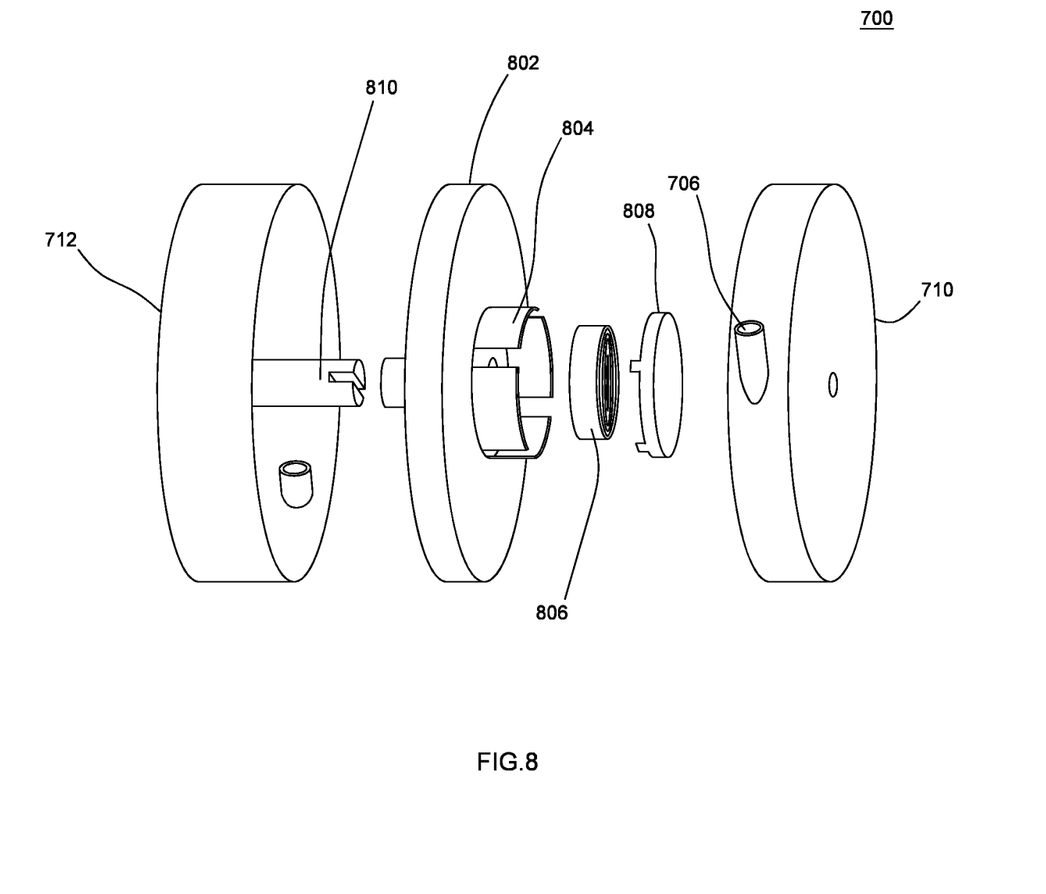
FIG. 8 shows an exploded view of a cable reel for using with a cable swipe cassette assembly, in accordance with some embodiments.

FIG. 7 shows a cable reel housing 700 for use with a cable swipe cassette assembly, in accordance with some embodiments. The housing 700 is intended to hold a reel on which a signal cable is wound and that can be drawn out of the housing and off the reel, or back into the housing onto the reel. The reel is shown in FIG. 8. The housing 700 has a generally cylindrically shaped body 702 in the form of a cylinder having a length that is less than its diameter, and thus resembles more of a puck shape. The housing has two halves 710, 712 that form opposing ends of the body 702, and which interface around the outside of the body 702, along the diameter of the body 702. The body can be attached to a connecting boss 704 that allows the body 702 to the attached to, or otherwise mounted on a medical device stand. Further, the body 702 has a cable inlet 708 through which one end of the cable passes and connects to the medical device. The body 702 also has a cable outlet 706 through which the cable passes from the reel inside the housing to a sensor or medical component that is monitored or controlled by the medical device. As shown here, the cable outlet 706 does not allow for a cable swipe cassette assembly (e.g. 500) to be mounted on the housing at the cable outlet 706, but in some embodiments, there is a feature at the cable outlet 706 that allows for the cable swipe cassette assembly to be mounted onto the housing 702. In cases where the cable swipe cassette assembly cannot be mounted directly on the reel housing 700, a bracket or other suitable structure is preferably used to hold the cable swipe cassette assembly in front of the cable outlet 706.

FIG. 8 shows an exploded view of a cable reel housing 700 for using with a cable swipe cassette assembly, in accordance with some embodiments. In addition to the housing portions 710, 712, there is shown in housing portion 712 an axial spindle 810 on which a rotatable reel member 802 is mounted. The reel member 802 is able to revolve around the spindle 810. The reel member 802 includes a spring basket 804 that is a made of several wall members that extend from the radial wall 803 around a central opening in the radial wall 803 through which the spindle 810 passes. The wall members can follow a circle centered around the central opening. A coil spring 806 is housed in the spring basket 804 and has an inner end of the coil attached to the spindle and the outer end of the coil attached to the reel member 802, such as the spring basket 804. Thus, when the reel member 802 is rotated, it loads the spring 806 and biases the spring to cause the reel member 802 to turn the opposite direction from that in which it is turned to load the spring 806. A cover 808 is placed over the spring 806 to hold the spring 806 in the basket 804, and can latch to the wall members of the basket 804 to retain the cover 808 on the basket 804. The spindle 810 can have a distal end that meet the radial wall of housing portion 710 to hold the reel member 802 between and within the two housing portions 710, 712.

A cable can be inserted through an opening in the center of the radial wall of housing portion 712, through the center of the reel member 802, the spring, 806 and cover 808 using a swivel connector that allows one portion of the cable to rotate relative to the other portion opposite the swivel connector. Alternatively, the swivel connector can be built into the reel at the center of the housing portion 712. A cable portion is wound around the basket 806, having an end fed through the cable outlet 706. Thus, when the cable is pulled through the cable outlet 706, it causes the reel member 802 to turn, which loads the spring 806. The reel 802 can be locked in place by a lever or similar interference structure, and once the cable is done being used, the lock can be removed, allowing the loaded spring to rotate the reel in the opposite direction and thereby drawing the cable back into the reel and around the basket 806.

Figure 9:
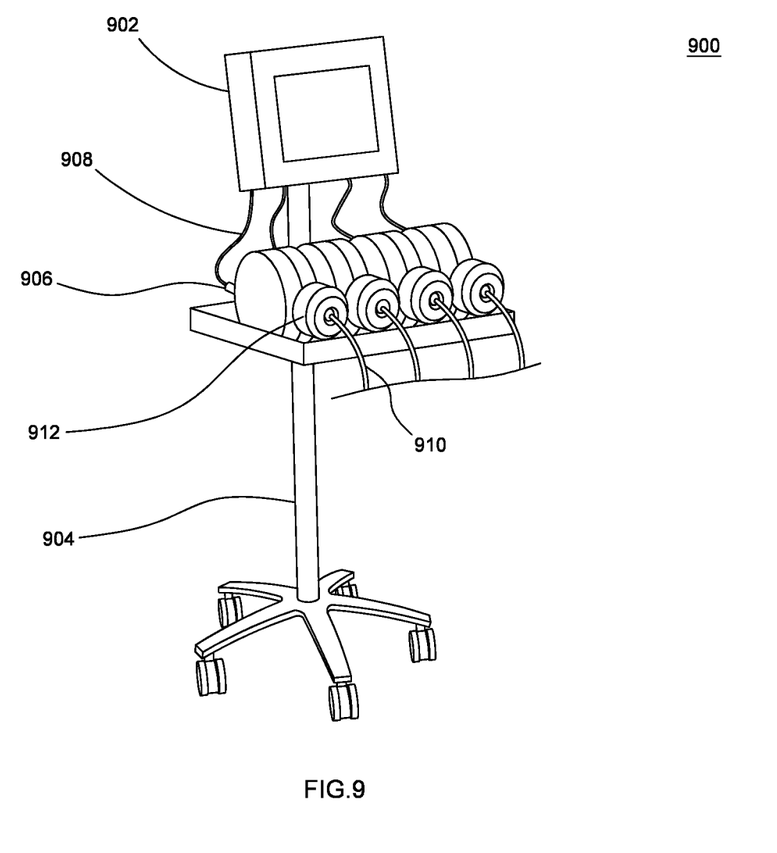
FIG. 9 shows a medical device stand using several cable reels, each with a cable swipe cassette, in accordance with some embodiments.

FIG. 9 shows a medical device stand system 900 using several cable reels, each with a cable swipe cassette, in accordance with some embodiments. The system 900 includes a medical device 902 that has a graphic display. The medical device 902 is mounted on the top of a stand 904, and specifically on the top of a central post of the stand 904. The stand 904 can have several casters or wheels so that the stand 904 can be mobile and moved from patient to patient as needed. The medical device 902 can monitor several physiological parameters of a patient through electromotive sensors that are coupled to specific channels of the medical device through cable assemblies. The cable assemblies each include a reel 906 on which a wound portion 910 of a cable stored, and wound on a reel member inside the reel 906. A static cable portion 908 is connected between the reel 906 and the medical device 902. The static cable portion 908 can be connected to the wound portion 910 through a swivel connector that allows the wound portion to rotate about the swivel connector without twisting the cable. A cable swipe cassette assembly 912 is attached or mounted at the cable outlet of each reel. The cable swipe cassette assembly 912 can be substantially the same as cable swipe assembly 500, and contains a puck that hold an antimicrobial fluid. As the cable 910 is moved through the puck in the cable swipe cassette assembly 912, the antimicrobial fluid is imparted to the exterior surface of the cable, thereby disinfecting that portion of the cable's exterior surface. Thus, when the medical device is used with a new patient, each cable for each reel can be drawn out and attached to a sensor or electrode, and when pulled out of the reel, the exterior surface of the cable is disinfected. This greatly reduces the chances of transmitting or carrying infectious agents to the patient or the patient's garments or bedding. And when the medical device 902 is no longer needed, the cables are allowed to reel back up, passing again through the puck and being coated with the antimicrobial material. Thus, for most patients, the cable 910 is disinfected twice; once when it is drawn back onto the reel after use with a prior patient, and then again when pulled out of the reel.

Figure 10:
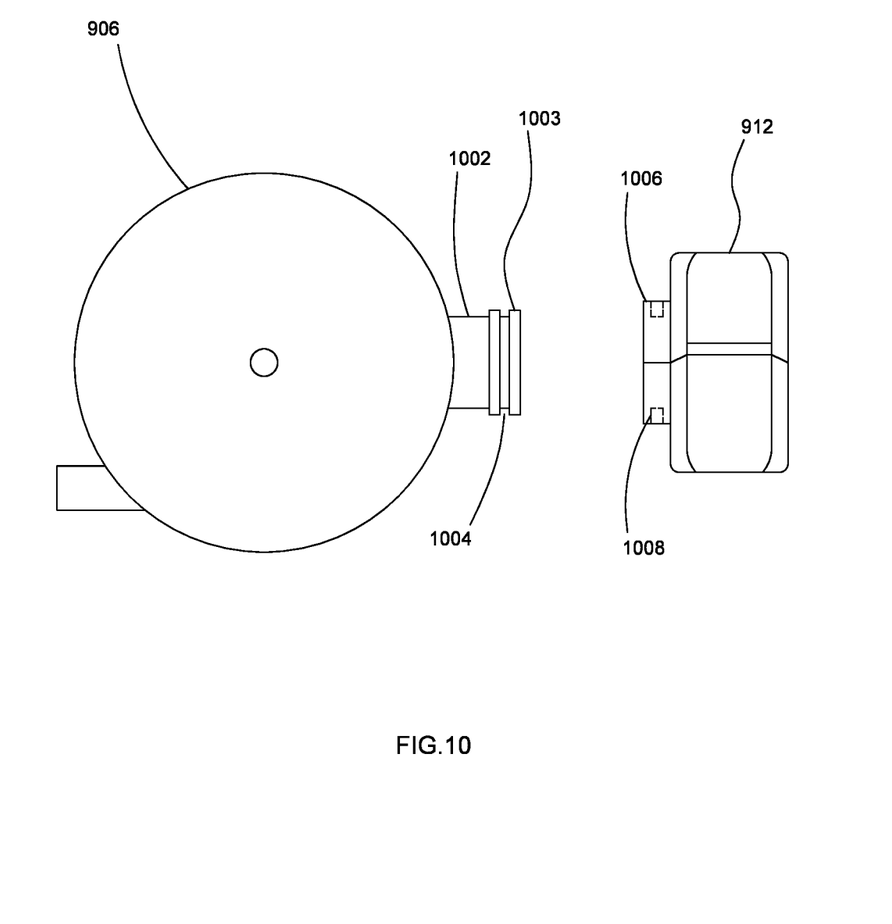
FIG. 10 shows a side view of a cable reel and a clamp on cable swipe cassette, separated, in accordance with some embodiments.
Figure 11:
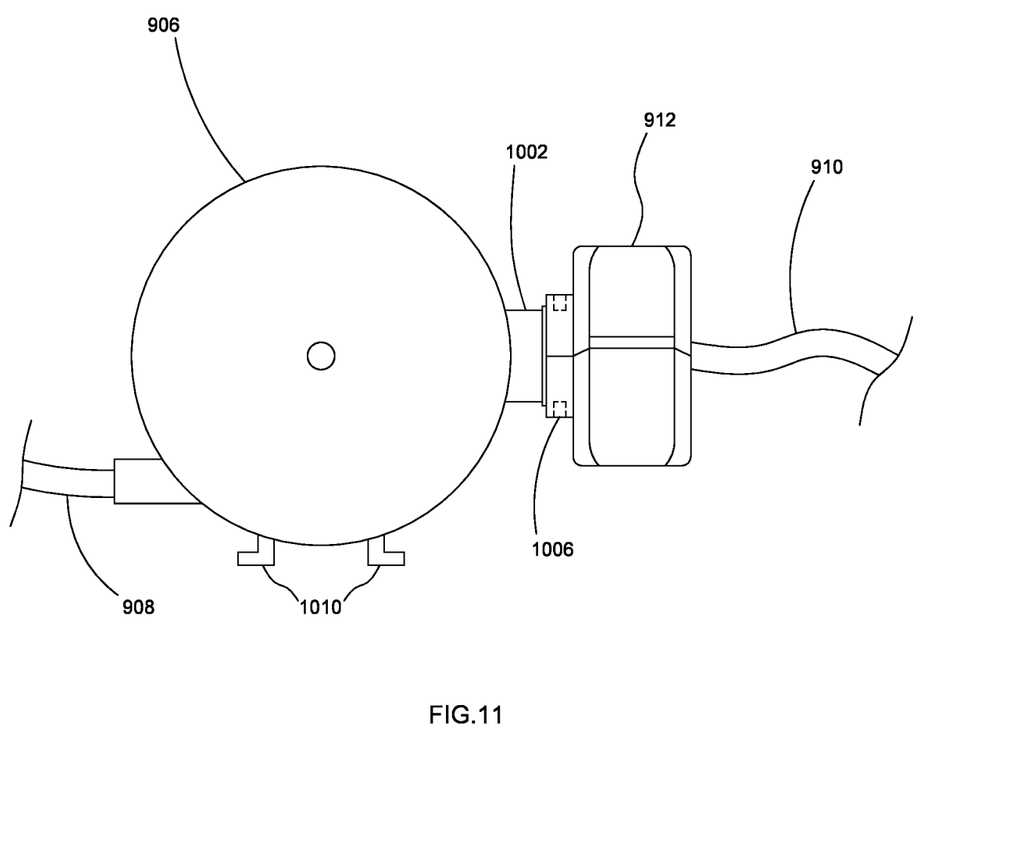
FIG. 11 shows a side view of a cable reel and a clamp on cable swipe cassette, with the cable swipe cassette clamped onto the cable reel, in accordance with some embodiments.

FIG. 10 shows a side view of a cable reel 906 and a clamp on cable swipe cassette 912, separated, and FIG. 11 shows a side view of the cable reel 906 and a clamp on cable swipe cassette 912, with the cable swipe cassette 912 clamped onto the cable reel, in accordance with some embodiments. In both figures the cable swipe cassette 912 is shown in a closed configuration. In FIG. 10 it can be seen that the cable reel 906 has a cable outlet 1002 that includes one or more annular ridges or shoulders 1003 around the cable outlet 1002. The cable swipe cassette 912 includes, on one side, an annular wall 1006 that extends outward from the side of the cable swipe cassette 912. Half of the annular wall is on the upper portion of the housing of the cable swipe cassette 912, and half is on the bottom portion of the housing of the cable swipe cassette 912. By opening the housing, as is shown for example in FIG. 5, the upper and lower portions of the annular wall 1006 come apart. Inside the annular wall 1006 is an annular ridge 1008 that is configured to fit over a first shoulder 1003 on the cable outlet 1002 of the cable reel 906 at location 1004. When the housing is then closed, the annular ridge 1008 is captured on the other side of shoulder 1003, creating a mechanical interference that prevents the housing from coming off the cable outlet 1002. FIG. 11 shows the cable swipe cassette 912 clamped onto the cable outlet 1002 with the reel cable portion 910 passing through the cable swipe cassette. The reel 906 can have feet 1010 or some other structure for connecting to a tray or other structure on the stand 904 (FIG. 9).

FIG. 12 shows a series of several cable swipes that all fit in the same cassette housing but which accommodate cables of different sizes, in accordance with some embodiments. There are three pucks 1202, 1204, 1206 shown. Each has the same outer diameter 1208, but the diameters of the bore through each of them, where the cable passes, can be different. Thus, the bore of puck 1202 has the smallest diameter D1, the bore of puck 1204 has a diameter D2 that is larger than D1, and the bore of puck 1206 has a diameter D3 that is larger still than D2. This allows different sized cables to be used with the same cable swipe cassette housing, and ensuring that the contact between the puck and the cable is neither too light or too heavy. If the contact is too light, then there may not be adequate distribution of the antimicrobial material to the cable's exterior surface. If the contact is too heavy, e.g. the bore is too small, then the drag on the cable between the material of the puck and cable's exterior surface may prevent the reel from drawing the cable back into the reel.

A cable wetting system has been disclosed in which a cable swipe cassette holds a puck that is made of a porous resilient material and there is a fluid disposed in the puck. A cable is placed into the cable swipe cassette so that the cable runs through bore through the puck. The puck is held in place, such as by a cable swipe cassette housing, so that the cable can be drawn through the puck, resulting in some of the fluid in the puck wetting the outer surface of the cable. In some embodiments the fluid can be an antimicrobial fluid, and the cable can be a cable for a medical device that is used to connect the medical device to a medical or physiological sensor on a patient. In some embodiments a portion of the cable can be stored on a reel, and drawn from the reel and through the puck when pulling the cable out for use. In some embodiments it is contemplated that the cable can be stored loosely, and drawn through the puck as needed.

What is claimed is:

1. A cable swipe cassette, comprising:
   a puck made of a porous resilient material, the puck having a bore through the puck from a first side to a second side opposite the first side; and
   a housing having an upper portion and a lower portion, each of the upper portion and the lower portion having a first side and a second side, wherein the housing is configured to enclose the puck therein between the first side and the second side of the upper portion and between the first side and the second side of the lower portion, and wherein an opening is formed at the first side of the upper portion and the lower portion that correspond with the bore through the puck at the first side of the puck, and an opposing opening is formed at the second side of the upper portion and the lower portion that corresponds with the bore through the puck at the second side of the puck, and wherein the housing is sized such that the puck is compressed by the housing when the housing is closed around the puck.

2. The cable swipe cassette of claim 1, wherein the upper portion and the lower portion are coupled together at a hinge.

3. The cable swipe cassette of claim 2, wherein the housing has a latch opposite the hinge to latch the upper and lower portions of the housing together.

4. The cable swipe cassette of claim 1, further comprising a fluid disposed in the puck.

5. The cable swipe cassette of claim 4, wherein the fluid is an antimicrobial fluid.

6. The cable swipe cassette of claim 1, wherein the puck further comprises a slot extending outward from the bore to a cylindrical surface of the puck.

7. The cable swipe cassette of claim 5, wherein the bore is configured to wet an external surface of a cable being drawn through the bore.

8. A disinfecting cable swipe cassette assembly for disinfecting an exterior surface of a cable, comprising:
   a puck made of a fluid absorbent material, the puck having a bore through the puck from a first side to a second side opposite the first side, and wherein a diameter of the bore is selected to be smaller than a diameter of the cable; and
   a housing having an upper portion and a lower portion, each of the upper portion and the lower portion having a first side and a second side, wherein the housing is configured to enclose the puck therein between the first side and the second side of the upper portion and between the first side and the second side of the lower portion, and wherein an opening is formed at the first side of the upper portion and the lower portion that correspond with the bore through the puck at the first side of the puck, and an opposing opening is formed at the second side of the upper portion and the lower portion that corresponds with the bore through the puck at the second side of the puck, and wherein the housing is sized such that the puck is compressed by the housing when the housing is closed.

9. The disinfecting cable swipe cassette assembly of claim 8, wherein the puck is made of a porous resilient material.

10. The disinfecting cable swipe cassette assembly of claim 8, further comprising the puck having a slot extending through the puck from the bore to an outside of the puck.

11. The disinfecting cable swipe cassette assembly of claim 8, further comprising a fluid disposed in the fluid absorbent material.

12. The disinfecting cable swipe cassette assembly of claim 11, wherein the fluid is an anti-microbial fluid.

13. The disinfecting cable swipe cassette assembly of claim 8, further comprising a hinge connecting the upper portion to the lower portion at a side of the housing between the first sides and the second sides of the upper and lower portions of the housing, and wherein the housing is made of a fluid impermeable material.

14. The disinfecting cable swipe cassette assembly of claim 13, further comprising a latch formed on the outside of the housing opposite the hinge.

\* \* \* \* \*